(12) United States Patent
Gysling (10) Patent No.: US 8,117,918 B2
(45) Date of Patent: Feb. 21, 2012

(54) METHOD AND APPARATUS FOR DETERMINING PIPEWALL THICKNESS USING ONE OR MORE ULTRASONIC SENSORS

(75) Inventor: Daniel L. Gysling, Glastonbury, CT (US)

(73) Assignee: Expro Meters, Inc., Wallingford, CT (US)

( * ) Notice: Subject to any disclaimer, the term of this patent is extended or adjusted under 35 U.S.C. 154(b) by 317 days.

(21) Appl. No.: 12/405,054

(22) Filed: Mar. 16, 2009

(65) Prior Publication Data

US 2009/0229364 A1 Sep. 17, 2009

Related U.S. Application Data

(60) Provisional application No. 61/036,689, filed on Mar. 14, 2008.

(51) Int. Cl.
*A61B 5/04* (2006.01)

(52) U.S. Cl. ............................................. 73/623; 73/627

(58) Field of Classification Search ..................... 73/623, 73/627–628
See application file for complete search history.

(56) References Cited

U.S. PATENT DOCUMENTS

| | | | |
|---|---|---|---|
| 5,009,103 A * | 4/1991 | Sato et al. | 73/597 |
| 5,460,046 A | 10/1995 | Maltby et al. | |
| 5,497,661 A | 3/1996 | Stripf | |
| 5,549,004 A | 8/1996 | Nugent | |
| 5,698,854 A | 12/1997 | Gupta | |
| 5,856,622 A | 1/1999 | Yamamoto et al. | |
| 6,261,233 B1 * | 7/2001 | Kantorovich | 600/454 |
| 6,763,698 B2 | 7/2004 | Greenwood | |
| 7,272,529 B2 * | 9/2007 | Hogan et al. | 702/171 |
| 7,330,797 B2 | 2/2008 | Bailey et al. | |
| 7,389,187 B2 | 6/2008 | Kersey et al. | |
| 2004/0250624 A1 * | 12/2004 | Abbate et al. | 73/597 |
| 2005/0172697 A1 | 8/2005 | Nozaki et al. | |
| 2006/0212261 A1 | 9/2006 | Glascock | |

FOREIGN PATENT DOCUMENTS

DE 4306119 9/1994

* cited by examiner

*Primary Examiner* — Max Noori
(74) *Attorney, Agent, or Firm* — O'Shea Getz P.C.

(57) ABSTRACT

A method for measuring the thickness of a pipe wall is provided. The method includes the steps of: 1) emitting ultrasonic signals into the pipe wall at one or more frequencies below 1 MHz and receiving reflected ultrasonic signals, and providing a sensor signal representative of the received reflected signals, including a first received reflected signal and a second received reflected signal; 2) providing a first model signal representative of the first received reflected signal and a second model signal representative of the second received reflected signal; 3) correlating the received reflected signals to the model signals, including varying a time delay between the model signals, until the model signals separated by the time delay substantially agree with the received reflected signals; and 4) determining the thickness of the pipe wall using the time delay.

24 Claims, 5 Drawing Sheets

METHOD AND APPARATUS FOR DETERMINING PIPEWALL THICKNESS USING ONE OR MORE ULTRASONIC SENSORS

CROSS-REFERENCE TO RELATED PATENT APPLICATIONS

This application claims the benefit of U.S. Provisional Patent Application No. 61/036,689 filed Mar. 14, 2008, which is hereby incorporated by reference herein in its entirety.

BACKGROUND OF THE INVENTION

1. Technical Field

This invention relates methods and apparatus for measuring the thickness of a pipe wall in general, and to methods and apparatus for measuring the thickness of a pipe wall noninvasively using ultrasonic sensors in particular.

2. Background Information

A common problem for pipe lines of all types is the potential for corrosion and wear on the interior surfaces of the wall over time, and the potential for rupture of the pipe wall as a result of the degradation of the wall caused by corrosion and/or wear. The problem is particularly acute for applications that pass a fluid flow containing abrasive particulates through the pipe. The wall degradation typically cannot be visually detected because the interior of the pipe is closed, and contains the fluid flow. Stopping the fluid flow and dismantling the pipe to gain access to the pipe interior is not practical.

It is known to use ultrasonic sensors to evaluate wall thickness. U.S. Pat. No. 5,549,004 discloses a "Hand Held Tube Wall Thickness Ultrasonic Measurement Probe and System" (the '004 Patent). According to the '004 Patent, most ultrasonic testing is performed at frequencies between 1 MHz and 25 MHz, and the preferred frequency for the disclosure of the '004 Patent is 5 MHz.

One of the problems with a hand held wall thickness sensing device is that it is very difficult over a period of time to accurately monitor the exact same positions around the circumference of the pipe. Changes in the measurement position corrupt data collected over time. Consequently, it is problematic, and likely not possible, to accurately determine pipe wall thickness degradation trends. In addition, such hand measurement devices represent a cost to the party maintaining the piping system.

In many of the applications where it is desirable to monitor pipe wall thickness, it is also desirable to measure fluid flow characteristics within the pipe. Ultrasonic flow meters that utilize an array of ultrasonic sensors provide a particularly useful and robust tool for sensing flow characteristics such as velocity and volumetric rate of the entire flow, and for the constituents in those fluid flows having multiple phases (e.g., oil, water, gas). It is advantageous in such flow meters to utilize ultrasonic sensors that operate at frequencies below 1 MHz, which frequencies are below the frequency range utilized by commercially available ultrasonic wall thickness measurement devices.

What is needed is an apparatus and method for measuring pipe wall thicknesses that utilizes ultrasonic sensors, and one that can utilize existing sensors deployed within existing ultrasonic flow meters.

SUMMARY OF THE INVENTION

According to an aspect of the present invention, a method for measuring the thickness of a pipe wall is provided. The method includes the steps of: 1) emitting ultrasonic signals into the pipe wall and receiving reflected ultrasonic signals, and providing a sensor signal representative of the received reflected signals, including a first received reflected signal and a second received reflected signal; 2) providing a first model signal representative of the first received reflected signal and a second model signal representative of the second received reflected signal; 3) correlating the received reflected signals to the model signals, including varying a time delay between the model signals, until the model signals separated by the time delay at least substantially agree with the received reflected signals; and 4) determining the thickness of the pipe wall using the time delay.

According to another aspect of the present invention, an apparatus for measuring a thickness of a pipe wall is provided that includes one or more ultrasonic sensors, an ultrasonic sensor processor, and a signal processor. The ultrasonic sensors are each operable to emit ultrasonic signals and receive reflected ultrasonic signals, and to provide a sensor signal representative of the received reflected signals, including a first received reflected signal and a second received reflected signal. The ultrasonic sensor processor is adapted to fire the one or more ultrasonic sensors, and to accept the signals from the sensors. The signal processor is adapted to include a first model signal representative of the first received reflected signal and a second model signal representative of the second received reflected signal. The signal processor is further adapted to correlate the received reflected signals to the model signals, including varying a time delay between the model signals until the model signals separated by the time delay substantially agree with the received reflected signals. The signal processor is further adapted to determine the thickness of the pipe wall using the time delay.

According to another aspect of the present invention, a method for measuring a thickness of a pipe wall is provided. The method comprises the steps of: 1) emitting ultrasonic signals into the pipe wall at a frequency corresponding to a wavelength that is equal to or greater than one third the thickness of the pipe wall, and receiving reflected ultrasonic signals, and providing a sensor signal representative of the received reflected signals, including a first received reflected signal and a second received reflected signal; 2) providing a first model signal representative of the first received reflected signal and a second model signal representative of the second received reflected signal; 3) correlating the received reflected signals to the model signals, including varying a time delay between the model signals, until the model signals separated by the time delay substantially agree with the received reflected signals; and 4) determining the thickness of the pipe wall using the time delay.

According to another aspect of the present invention, a method for measuring a thickness of a pipe wall with a flow meter having an array of ultrasonic sensors, which meter is operable to measure characteristics of a fluid flow within the pipe, is provided. The method comprises the steps of: 1) emitting ultrasonic signals using at least one of the sensors within the array and receiving reflected ultrasonic signals, and providing a sensor signal representative of the received reflected signals, including a first received reflected signal and a second received reflected signal; 2) providing a processor adapted to have a first model signal representative of the first received reflected signal and a second model signal representative of the second received reflected signal; 3) correlating the received reflected signals to the model signals using the processor, including varying a time delay between the model signals, until the model signals separated by the time delay substantially agree with the received reflected signals;

and 4) determining the thickness of the pipe wall based on the time delay using the processor.

According to another aspect of the present invention, a method for measuring the thickness of a pipe wall, comprising the steps of: 1) emitting an ultrasonic signal into the pipe wall at a frequency and receiving reflected ultrasonic signals resulting from the emitted signal, wherein the frequency is such that the reflected ultrasonic signals are not localized in time, and providing a sensor signal representative of the received reflected signals, including a first received reflected signal and a second received reflected signal; 2) providing a first model signal representative of the first received reflected signal and a second model signal representative of the second received reflected signal; 3) correlating the received reflected signals to the model signals, including varying a time delay between the model signals, until the model signals separated by the time delay substantially agree with the received reflected signals; and 4) determining the thickness of the pipe wall using the time delay.

One of the advantages provided by the present method and apparatus is that it provides a means to measure the wall thickness of a pipe using ultrasonic sensors typically deployed in flow meters. As a result, it provides a means for determining pipe wall thickness using common hardware. In addition, in certain embodiments it provides a means to measure pipe wall thickness that leverages hardware used for other purposes; e.g., flow meters, etc.

Another advantage of the present invention is that it can determine the thickness of a pipe wall using an ultrasonic sensor operating a lower frequency that prior art devices. The lower frequency sensor provides a more representative average wall thickness than devices using higher frequency (e.g., 5 MHz) ultrasonic sensors. The higher frequency sensors are more susceptible to imperfections within the pipe wall and variations in the pipe wall surfaces, which imperfections can lead to erroneous wall thickness data.

The foregoing and other objects, features and advantages of the present invention will become more apparent in light of the following drawings and detailed description of the present invention.

BRIEF DESCRIPTION OF THE DRAWINGS

Referring now to the drawings, the foregoing and other features and advantages of the present invention will be more fully understood from the following detailed description of illustrative embodiments, taken in conjunction with the accompanying drawings in which like elements are numbered alike.

DETAILED DESCRIPTION OF THE INVENTION

Figure 1:
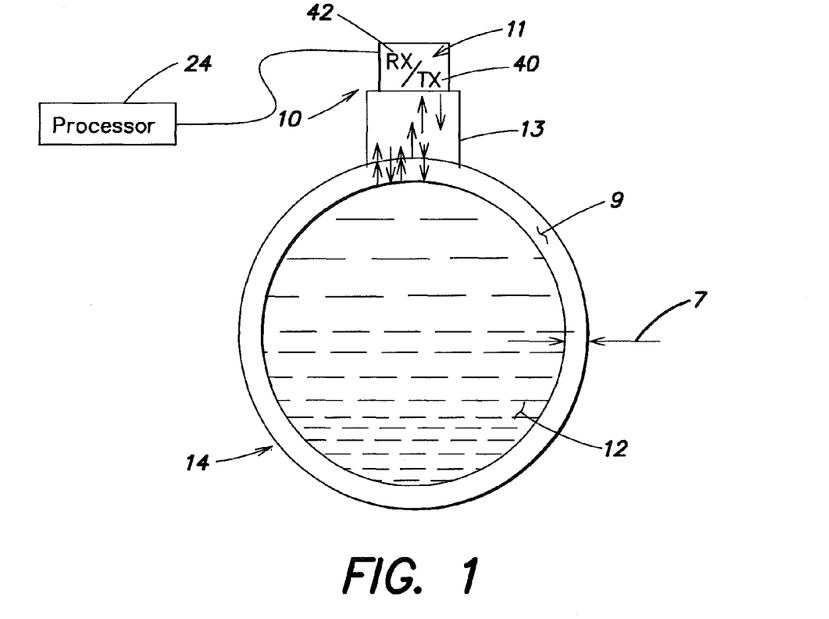
FIG. 1 is a diagrammatic view of an ultrasonic pipe wall thickness measuring device according to an aspect of the present invention.

Referring to FIG. 1, according to the present invention, a method and an apparatus 5 for non-invasively determining the thickness 7 of a wall 9 of a pipe 14 is provided. The apparatus 10 includes one or more ultrasonic sensors 11 and a signal processor 24 for processing the signals transmitted from the sensors 11.

In some embodiments, a sensor shoe 13 is disposed between the sensors 11 and the pipe wall 9. The shoe 13 provides an ultrasonic signal path between the sensors 11 and the pipe wall 9, and a platform for mounting the sensors 11 to the pipe 14. The shoe 13 is not limited to any particular material or configuration. An example of an acceptable shoe 13 is one consisting of Ultem®, which is a polyetherimide (PEI) thermoplastic material made by SABIC.

The ultrasonic sensors 11 are configured in a pulse/echo configuration. Each sensor 11 includes a transmitter portion 40 (Tx) and a receiver portion 42 (Rx). The transmitter 40 is operable to selectively transmit an ultrasonic signal in a direction that is substantially normal to the pipe wall 9; i.e., a direction where the signal traverses across the pipe wall 9. The receiver portion 42 is operable to receive ultrasonic signals reflected back at the sensor 11, which signals originate from the signal transmitted from the sensor 11. The transmitted signals propagate through the shoe 13, pipe wall 9, and fluid 12 traveling within the pipe 14, in a direction substantially orthogonal to the direction of fluid flow 12 within the pipe 14. Reflected signals (also referred to as "echo signals") are created at each interface (e.g., shoe/wall, near wall/fluid, fluid/far wall) within the signal path when the incident transmitted signals reaches the interface. The reflected signals travel in the opposite direction of the incident signal. The ultrasonic sensors 11 used according to certain aspects of the present invention have a frequency response of less than 1 MHz, which frequency is favorable for both determining the thickness 7 of a pipe wall 9 and for use in flowmeters measuring flow characteristics within a multiphase fluid. In many industries (e.g., oil and gas) the fluid flow contained within the pipe is a multiphase fluid flow, and may contain particulate matter, or it may be a slurry. In many of those industries, the pipe wall thicknesses 7 that are of sufficient concern to be tested are typically in the range of 0.1 to 2.0 inches thick. As indicated above, a low frequency ultrasonic sensor 11 (e.g., one operating at a frequency associated with a wavelength that is equal to or greater than about one-third of the pipe wall thickness 7) provides advantages in the monitoring of pipe wall thicknesses in those applications. For thinner wall pipes, a higher frequency sensor can be used. The ultrasonic sensors 11 may be controlled to provide different signal forms (e.g., pulsed, chirped, or continuous signals) through the fluid flow 12. Pulse/echo configuration ultrasonic sensors are known in the art (e.g., from manufacturers such as Krautkramer). The ultrasonic sensor 11 may be implemented as a single sensor, or it may be one of an array of sensors 11.

Figure 2:
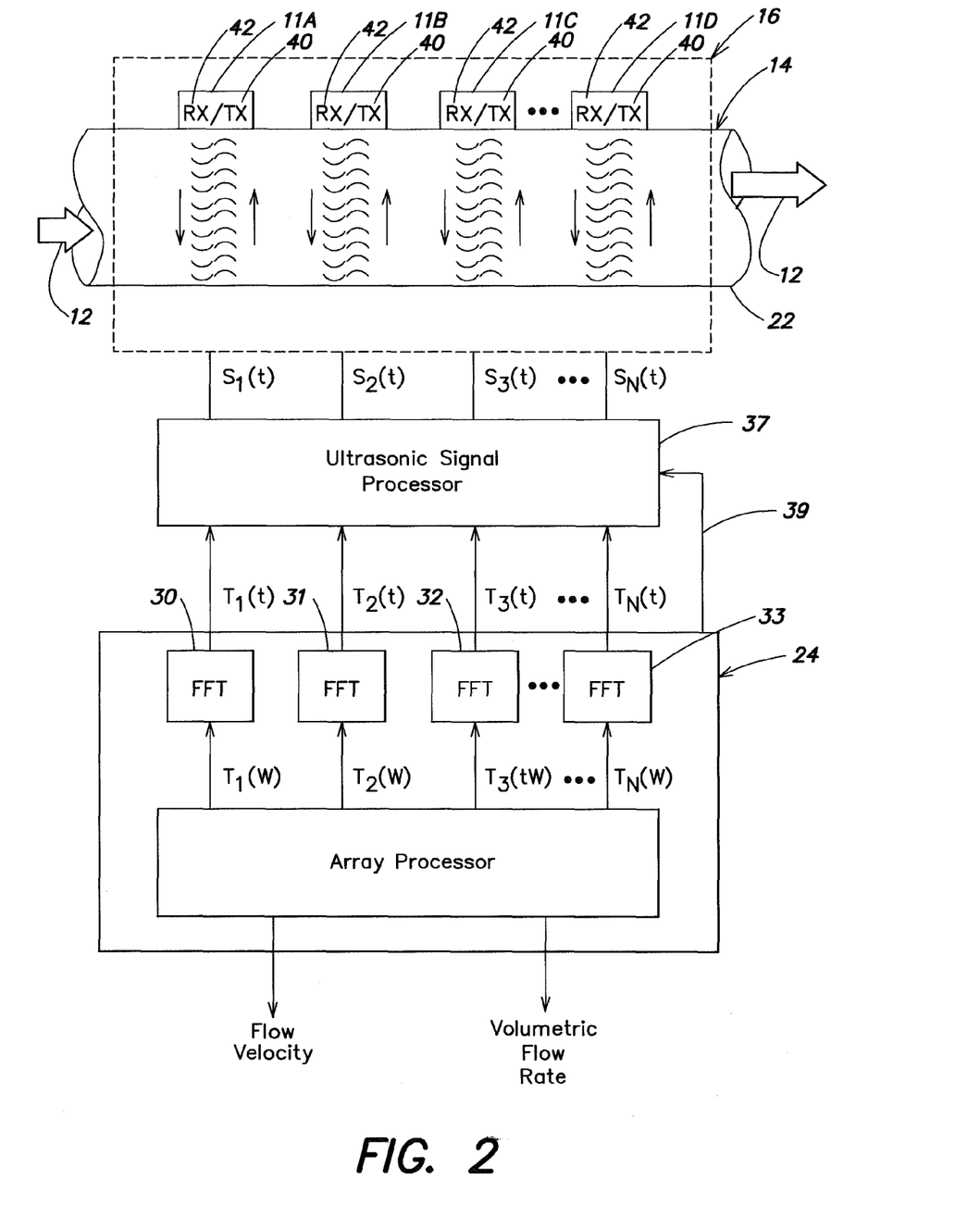
FIG. 2 is a schematic illustration of a flow measuring system for providing a density, composition, velocity and/or volumetric flow rate of the mixture in accordance with the present invention.

As an example, FIG. 2 illustrates a flow meter 10 having an array 16 of ultrasonic sensor units 11A-11D. Each sensor unit comprises a single ultrasonic sensor 11 having a transmitter portion 40 (Tx) and a receiver portion 42 (Rx). The sensor units 11A-11D are spaced axially along the outer surface 22 of a pipe 14 having a process flow 12 propagating therein. When operating as part of a flow meter, each ultrasonic sensor 11A-11D measures a transit time (i.e., time of flight (TOF), or phase modulation) of an ultrasonic signal propagating through the fluid flow within 12. The ultrasonic signals actually propagate through the fluid flow 12 a first time, reflect off of the orthogonally opposite pipe wall, and then propagate through the fluid flow 12 a second time, after which they are sensed by the receiver portion 42. The signal transit time measurement, and variations thereof, are indicative of the flow and coherent properties that convect with the flow within the pipe (e.g., vortical disturbances, inhomogenieties within the flow, temperature variations, bubbles, particles, pressure disturbances), which are indicative of the velocity of the process flow 12.

In flow meter operation mode, an ultrasonic signal processor 37 fires the transmitters 40 in response to a firing signal 39 from a processor 24 and receives the ultrasonic output signals $S_{1(t)}$-$S_{N(t)}$ from the receivers 42. The signal processor 37 processes the data from each of the sensor units 11A-11D to provide an analog or digital output signal $T_{1(t)}$-$T_{N(t)}$ indicative of the time of flight or transit time of the ultrasonic signal through the fluid 12. The ultrasonic signal processor 37 may also provide an output signal indicative of the amplitude (or attenuation) of the ultrasonic signals. One such ultrasonic signal processor is model no. USPC 2100, manufactured by Krautkramer Ultrasonic Systems. Measuring the amplitude of ultrasonic signal is particularly useful and works best for measuring the velocity of a fluid that includes a substance in the flow (e.g., multiphase fluid or slurry).

As stated above, one or more sensors 11 (e.g., the ultrasonic sensors 11A-11D disposed in the flow meter array 16 described above) are utilized to determine the thickness 7 of the pipe wall 9 to which they are directly or indirectly attached. To simplify the explanation provided below of the signal interaction relative to the shoe 13 and the near pipe wall 9, the sensor transmitted signals are discussed in the context of a single transmitted signal. In most applications, however, the sensor(s) periodically (e.g., chirp or pulse) or continuously transmit signals, which signals produce a convolution of received signals that are identified and distinguished via signal processing. The functionality of the signal processing described herein may be implemented using hardware, software, firmware, or a combination thereof, although the scope of the invention is not intended to be limited to any particular embodiment thereof. In a typical software implementation, the processors 24, 37 may include one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation. The scope of the invention includes the processors 24, 37 as stand alone modules, as shown, or alternatively in the combination with each other or other circuitry.

Figure 3:
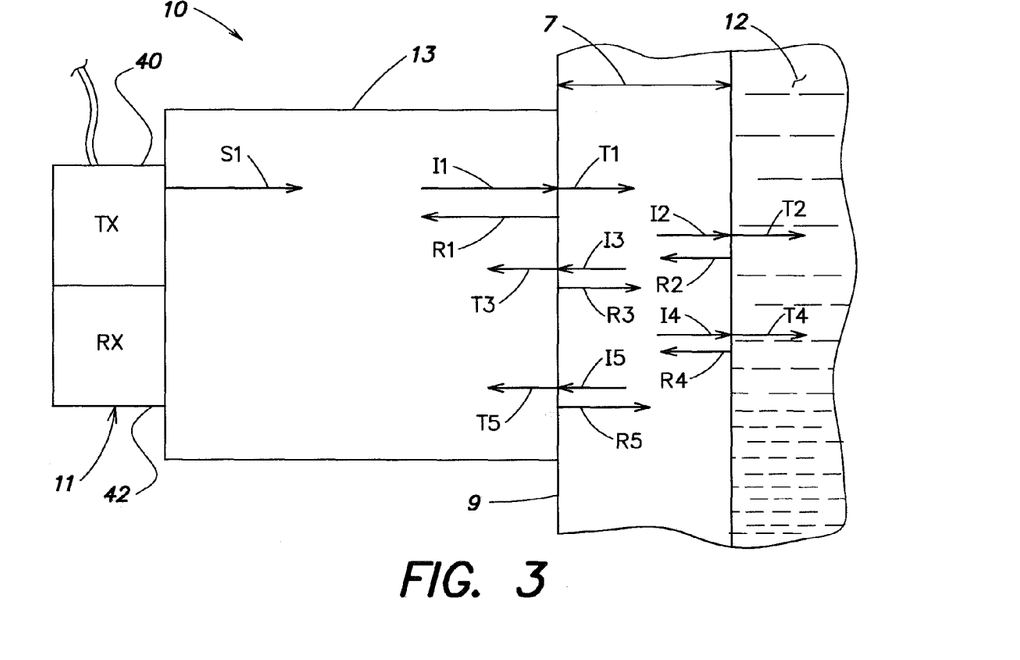
FIG. 3 is a diagrammatic illustration of signal paths from a sensor, through a sensor shoe and a pipe wall.

In the diagrammatic view shown in FIG. 3, the transmitter 40 emits a signal S1 into the shoe 13 and the receiver 42 subsequently receives echo signals resulting from the initial signal S1. The echo signals are created at each interface between different bodies 13, 9, 12, which bodies typically consist of different materials; e.g., shoe/pipe, pipe/fluid, fluid/pipe, etc. The impedance discontinuities present at each interface cause the reflected signals. At each interface, the signals can be represented as an incident signal wave (the signal that initially arrives at the interface through the first body), a transmitted signal wave (the signal that continues through the interface and into the second body), and a reflected signal wave (the signal that travels back through the first body in the direction opposite the direction of the incident signal).

The initial signal S1 travels through the shoe 13 and upon reaching the shoe/pipe wall interface as incident signal wave I1, creates reflected signal wave R1 and transmitted signal wave T1. R1 travels in a direction opposite I1 (i.e., back toward the receiver), and transmitted signal wave T1 enters the pipe wall 9. The time difference between the initial signal S1 and when R1 is received by the sensor receiver 42 is indicative of the time required for the signal to traverse the shoe 13 twice.

At the fluid flow/pipe interface, transmitted signal wave T1 is characterized as incident signal wave I2. The arrival of I2 creates reflected signal wave R2 and transmitted signal wave T2. R2 travels in a direction opposite I2 (i.e., back toward the receiver), and transmitted signal wave T2 enters the fluid flow within the pipe. At the pipe wall/shoe interface, reflected signal wave R2 is characterized as incident signal wave I3. The arrival of I3 creates reflected signal wave R3 and transmitted signal wave T3. R3 travels in the direction opposite that of I3 (i.e., toward the fluid flow) and T3 enters the shoe 13 and is subsequently sensed by the sensor receiver. The time difference (TAU1) between the arrival of R1 and T3 at the sensor receiver is representative of the signal traversing both the shoe 13 and the pipe wall 9 twice.

At the pipe wall/fluid flow interface, R3 is characterized as incident signal wave I4. The arrival of I4 creates reflected signal wave R4 and transmitted signal wave T4. R4 travels in a direction opposite the direction of I4 (i.e., back toward the receiver), and T4 enters the fluid flow. At the pipe wall/shoe interface, reflected signal wave R4 is characterized as incident wave I5. The arrival of I5 creates reflected signal wave R5 and transmitted signal wave T5. R5 travels in the direction opposite that of I5 (i.e., toward the fluid flow) and T5 enters the shoe 13 and is subsequently sensed by the sensor receiver. The time difference (TAU2) between the arrival of T3 and T5 at the sensor receiver is representative of the signal traversing the shoe 13 and the pipe wall 9 twice.

Figure 4:
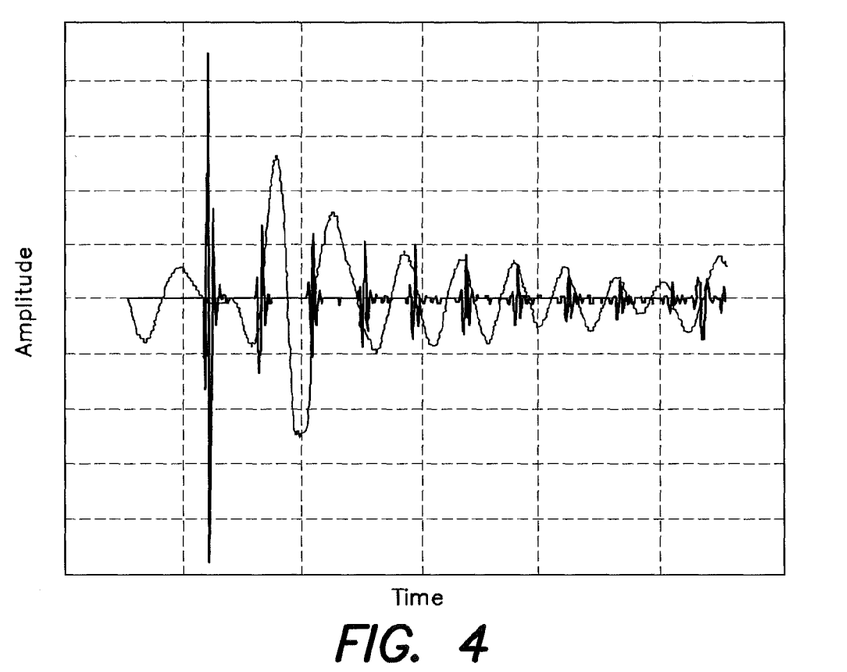
FIG. 4 is a graph illustrating a convolution of sensed ultrasonic signals from an ultrasonic sensor operating at 500 kHz.

As stated above, the sensor 11 receives a convolution of echo signals that must be identified and distinguished via signal processing. FIG. 4 illustrates an example of a convolution of echo signals, including signals that overlap in time, which may be also described as signals that are not localized in time. To identify those received reflected signals that can be used to determine the pipe wall thickness 7, the present invention uses model waveforms that are representative of certain received reflected signals (e.g., R1, T3, and T5) that have traversed the pipe wall 9. The model waveforms are associated with particular sensors 11. The signal processing described herein discusses model signal waveforms representative of reflected signals R1, T3, and T5. The present invention is not, however, limited to processing these particular reflected waveforms.

Figure 5:
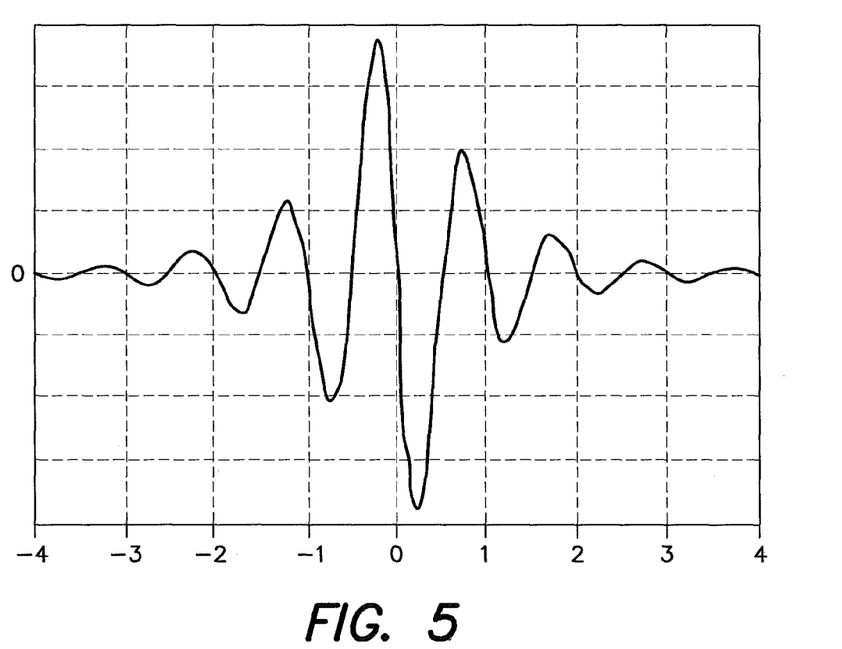
FIG. 5 is a diagrammatic view of a model reflected signal waveform for an R1 reflected signal.
Figure 6:
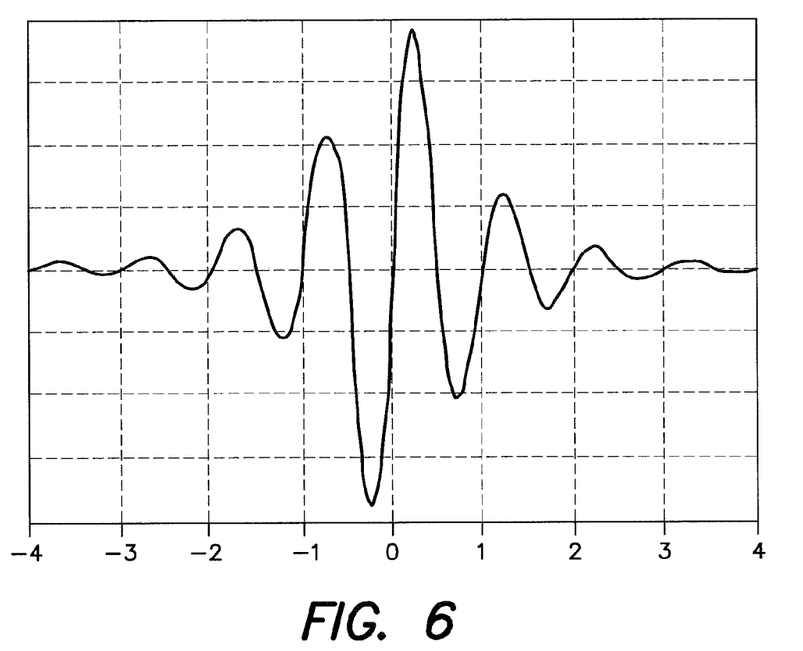
FIG. 6 is a diagrammatic view of a model reflected signal waveform for a T3 reflected signal.

According to one aspect of the present invention, the model waveforms can be modeled from data empirically collected (e.g., by testing) using the same (or similar) sensors operating at the wavelength(s) that are to be used during actual pipe wall thickness sensing. The empirical process includes operating the sensor to transmit signals through the shoe 13 and a pipe wall 9 (or a plate of the same material) and sensing the reflected signals (e.g., R1, T3, T5) and using those sensed reflected signals as the basis for constructing a model waveform for each reflected signal. The model waveforms are subsequently stored within the processor 24 for use in signal processing as will be described below. FIG. 5 illustrates a model waveform for R1 and FIG. 6 illustrates a model waveform for T3, both created using a 500 kHz (0.5 MHz) ultrasonic sensor.

Figure 7:
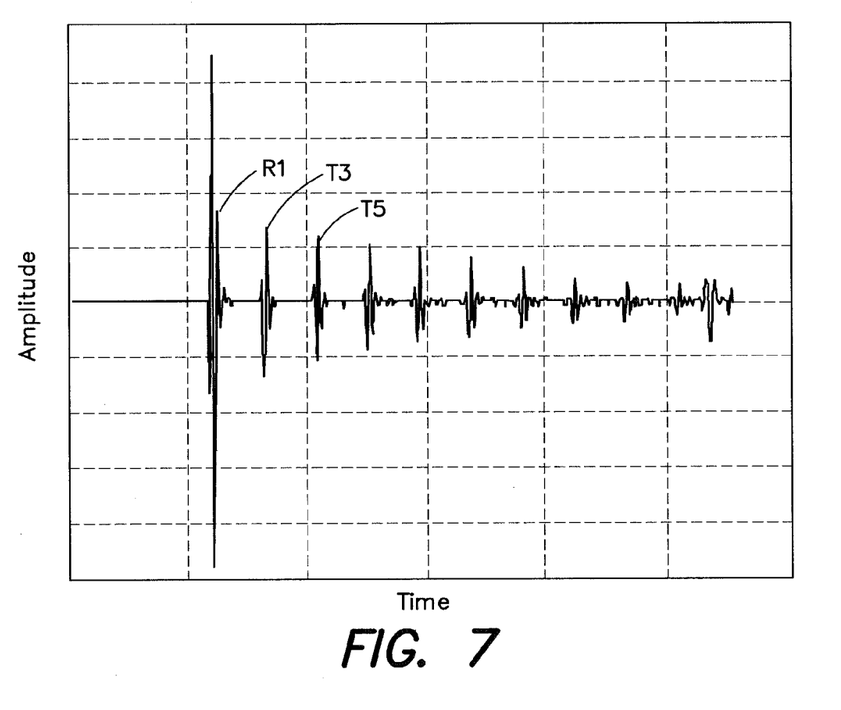
FIG. 7 is a graph illustrating sensed ultrasonic signals from an ultrasonic sensor operating at 5 MHz.

In an alternative aspect, model waveforms can be empirically constructed using a sensor operating at a wavelength other than that to be used during actual pipe wall thickness testing. The basic waveform of the reflected signal is assumed to be frequency independent within the range of sensor frequencies used for ultrasonic fluid flow testing, and the materials through which the ultrasonic signals propagate are assumed to have acoustic properties that are frequency independent. Consequently, a model reflected signal waveform can be constructed using sensors 11 operating at a variety of different frequencies. Ultrasonic sensors operating at about 5 MHz, for example, produce echo signals that are well localized in time, and therefore easily identifiable. FIG. 7 illustrates signals well localized in time produced using a 5 MHz ultrasonic sensor. The higher frequency reflected signals (e.g., R1, T3, T5) can be dilated to match the observed dominate transducer frequency of the actual type of transducer to be used (e.g., below 1 MHz). The dilated reflected signals are subsequently stored within the processor and utilized as model waveforms within the signal processing.

In an alternative aspect, model waveforms are empirically constructed using a test apparatus that uses the same (or similar) sensor operating at the wavelength(s) that are to be used during actual pipe wall thickness sensing. In this aspect, a shoe 13 is utilized having a thickness that is large enough such that the reflected signals R1 and T3 are received with sufficient time separation to enable independent measurement; e.g., the receiving periods of the reflected signals do not overlap. The independent measurement of the signals increases the accuracy of the model waveforms created for R1 and T3. The model waveforms are subsequently stored within the processor for use in signal processing.

Figure 8:
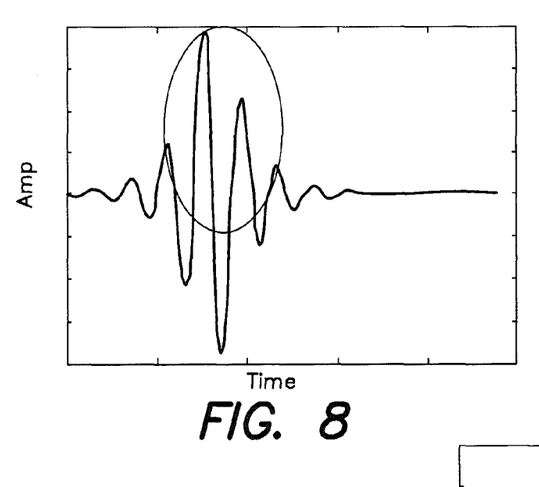
FIG. 8 is a sensed signal waveform at a delay time of TAU1.
Figure 9:
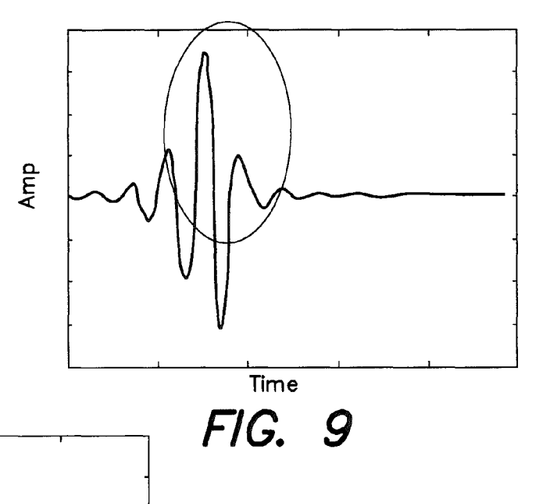
FIG. 9 is a sensed signal waveform at a delay time of TAU2.
Figure 10:
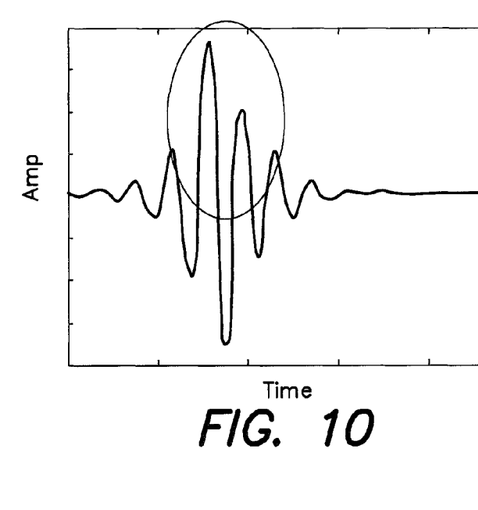
FIG. 10 is a sensed signal waveform at a delay time of TAU3.

The processor 24 is adapted to utilize an optimization procedure that correlates the model signal waveforms and selected time delay values (i.e., TAU values) to the reflected signals received by the sensor 11. For example, the transmitter 40 emits a signal into the shoe 13 and reflected signals are received by the receiver 42. The optimization procedure correlates the models to the received reflected signals to create a best fit of the model R1 signal waveform and the model T3 signal waveform amongst the sensed reflected signals by varying the time delays between the model waveforms. The time delay associated with the best fit of model waveforms R1 and T3 is representative of a signal that has traversed the pipe wall thickness 7 twice. For example, FIGS. 8-10 illustrate sensed reflected wave forms at three different time delay values (TAU1—FIG. 8, TAU2—FIG. 9, TAU3—FIG. 10). The waveform in FIG. 9 at a time delay value of TAU2 best fits the waveform of the recorded reflected signal. The pipe wall thickness 7 is determined using the time delay value (e.g., TAU2) associated with the best fit of model waveforms and the sensed reflected signals, and the speed of sound within the shoe material and the pipe wall 9 materials. The thickness of the shoe 13 is known and constant, and consequently the time it takes the ultrasonic signal to traverse the shoe 13 is constant and can be determined. The pipe wall thickness 7 is determinable from the time delay value less the travel time of the signal within the shoe 13. Optimization procedures operable to compare waveforms are known in the art, and the present invention is not limited to any particular optimization routine. For example, as an alternative to the above described optimization procedure wherein the signal waveforms are "visually" compared to one another, the optimization procedure can create a best fit between the received reflected signals and the model signal waveforms using a mathematical algorithm.

FIGS. 1 and 2 diagrammatically illustrate ultrasonic sensors 11 mounted on a pipe wall 9, at a particular circumferential position. In applications where a pipe wall 9 is likely to erode uniformly around the circumference of the pipe, a sensor located at a single circumferential position is likely adequate to provide the requisite pipe wall thickness 7 information. In applications where a pipe wall 9 is likely to erode randomly around the circumference of the pipe, or if the erosion pattern is unknown, a plurality of sensors 11 can be disposed around the circumference of the pipe to provide the requisite pipe wall thickness 7 information.

Although the invention has been described and illustrated with respect to exemplary embodiments thereof, the foregoing and various other additions and omissions may be made therein and thereto without departing from the spirit and scope of the present invention.

What is claimed is:

1. A method for measuring the thickness of a pipe wall, comprising the steps of:
   emitting ultrasonic signals into the pipe wall at one or more frequencies below 1 MHz and receiving reflected ultrasonic signals, and providing a sensor signal representative of the received reflected signals, including a first received reflected signal and a second received reflected signal;
   providing a first model signal representative of the first received reflected signal and a second model signal representative of the second received reflected signal;
   correlating the received reflected signals to the model signals, including varying a time delay between the model signals, until the model signals separated by the time delay substantially agree with the received reflected signals; and
   determining the thickness of the pipe wall using the time delay.

2. The method of claim 1, wherein the step of emitting ultrasonic signals is performed using one or more ultrasonic sensors, each mounted on a shoe which is in contact with the pipe wall.

3. The method of claim 2, wherein the first model signal and the second model signal are modeled using data empirically collected using one or more test ultrasonic sensors that are the same type as the one or more ultrasonic sensors.

4. The method of claim 3, wherein the one or more test ultrasonic sensors are mounted on test shoes, each of which is substantially similar to the shoe on which each sensor is mounted.

5. The method of claim 3, wherein each of the one or more test ultrasonic sensors is mounted on a test shoe that has a thickness through which signals traverse that is large enough such that the first received reflected signal and the second received reflected signal are received with a time separation that permits the first received reflected signal and the second received reflected signal to be measured independent of one another.

6. The method of claim 2, wherein the first model signal and the second model signal are modeled using data empirically collected using one or more test ultrasonic sensors operated at a frequency greater than 1 MHz.

7. A method for measuring the thickness of a pipe wall, comprising the steps of: :
   emitting ultrasonic signals into the pipe wall at one or more frequencies below 1 MHz and receiving reflected ultrasonic signals, and providing a sensor signal representative of the received reflected signals, including a first received reflected signal and a second received reflected signal;

providing a first model signal representative of the first received reflected signal and a second model signal representative of the second received reflected signal;

correlating the received reflected signals to the model signals, including varying a time delay between the model signals, until the model signals separated by the time delay substantially agree with the received reflected signals; and determining the thickness of the pipe wall using the time delay;

wherein the step of correlating the received reflected signals to the model signals, includes iteratively comparing a waveform of the received reflected signals to a waveform of the model signals using different values of the time delay.

8. A method for measuring the thickness of a pipe wall, comprising the steps of:

emitting ultrasonic signals into the pipe wall at one or more frequencies below 1 MHz and receiving reflected ultrasonic signals, and providing a sensor signal representative of the received reflected signals, including a first received reflected signal and a second received reflected signal;

providing a first model signal representative of the first received reflected signal and a second model signal representative of the second received reflected signal;

correlating the received reflected signals to the model signals, including varying a time delay between the model signals, until the model signals separated by the time delay substantially agree with the received reflected signals; and determining the thickness of the pipe wall using the time delay;

wherein the step of correlating the received reflected signals to the model signals includes mathematically comparing a waveform of the received reflected signals to a waveform of the model signals.

9. An apparatus for measuring a thickness of a pipe wall, comprising:

one or more ultrasonic sensors, each operable to emit ultrasonic signals and receive reflected ultrasonic signals, and to provide a sensor signal representative of the received reflected signals, including a first received reflected signal and a second received reflected signal;

an ultrasonic sensor processor adapted to fire the one or more ultrasonic sensors at one or more selected frequencies below 1 MHz, and to accept the signals from the sensor;

a signal processor adapted to include a first model signal representative of the first received reflected signal and a second model signal representative of the second received reflected signal, and adapted to correlate the received reflected signals to the model signals, including varying a time delay between the model signals, until the model signals separated by the time delay substantially agree with the received reflected signals, and determine the thickness of the pipe wall using the time delay.

10. The apparatus of claim 9, wherein each sensor is mounted on a shoe which is in contact with the pipe wall.

11. The apparatus of claim 10, wherein the first model signal and the second model signal are modeled using data empirically collected using one or more test ultrasonic sensors that are the same type as the one or more ultrasonic sensors.

12. The apparatus of claim 10, wherein the first model signal and the second model signal are modeled using data empirically collected using one or more test ultrasonic sensors operated at a frequency greater than 1 MHz.

13. An apparatus for measuring a thickness of a pipe wall, comprising:

one or more ultrasonic sensors, each operable to emit ultrasonic signals and receive reflected ultrasonic signals, and to provide a sensor signal representative of the received reflected signals, including a first received reflected signal and a second received reflected signal;

an ultrasonic sensor processor adapted to fire the one or more ultrasonic sensors at one or more selected frequencies below 1 MHz, and to accept the signals from the sensor; and a signal processor adapted to include a first model signal representative of the first received reflected signal and a second model signal representative of the second received reflected signal, and adapted to correlate the received reflected signals to the model signals, including varying a time delay between the model signals, until the model signals separated by the time delay substantially agree with the received reflected signals, and determine the thickness of the pipe wall using the time delay;

wherein the signal processor is adapted to compare a waveform of the received reflected signals to a waveform of the model signals using different values of the time delay in the process of correlating the received reflected signals to the model signals.

14. A method for measuring a thickness of a pipe wall, comprising the steps of:

emitting ultrasonic signals into the pipe wall at a frequency corresponding to a wavelength that is equal to or greater than one third the thickness of the pipe wall, and receiving reflected ultrasonic signals, and providing a sensor signal representative of the received reflected signals, including a first received reflected signal and a second received reflected signal;

providing a first model signal representative of the first received reflected signal and a second model signal representative of the second received reflected signal;

correlating the received reflected signals to the model signals, including varying a time delay between the model signals, until the model signals separated by the time delay substantially agree with the received reflected signals; and determining the thickness of the pipe wall using the time delay.

15. The method of claim 14, wherein each sensor is mounted on a shoe which is in contact with the pipe wall.

16. The method of claim 15, wherein the first model signal and the second model signal are modeled using data empirically collected using one or more test ultrasonic sensors that are the same type as the one or more ultrasonic sensors.

17. The method of claim 16, wherein the one or more test ultrasonic sensors are mounted on test shoes, each of which is substantially similar to the shoe on which each sensor is mounted.

18. The method of claim 16, wherein each of the one or more test ultrasonic sensors is mounted on a test shoe that has a thickness through which signals traverse that is large enough such that the first received reflected signal and the second received reflected signal are received with a time separation that permits the first received reflected signal and the second received reflected signal to be measured independent of one another.

19. The method of claim 14, wherein the frequency corresponds to a wavelength that is equal to or greater than about 0.1 inches.

20. A method for measuring a thickness of a pipe wall with a flow meter having an array of ultrasonic sensors, which meter is operable to measure characteristics of a fluid flow within the pipe, comprising the steps of:
   emitting ultrasonic signals at one or more frequencies below 1 MHz using at least one of the sensors within the array and receiving reflected ultrasonic signals, and providing a sensor signal representative of the received reflected signals, including a first received reflected signal and a second received reflected signal;
   providing a first model signal representative of the first received reflected signal and a second model signal representative of the second received reflected signal;
   correlating the received reflected signals to the model signals, including varying a time delay between the model signals, until the model signals separated by the time delay substantially agree with the received reflected signals; and
   determining the thickness of the pipe wall based on the time delay using the processor.

21. The method of claim 20, wherein the step of emitting ultrasonic signals is performed using one or more ultrasonic sensors, each mounted on a shoe which is in contact with the pipe wall.

22. The method of claim 21, wherein the first model signal and the second model signal are modeled using data empirically collected using one or more test ultrasonic sensors that are the same type as the one or more ultrasonic sensors.

23. The method of claim 22, wherein the one or more test ultrasonic sensors are mounted on test shoes, each of which is substantially similar to the shoe on which each sensor is mounted.

24. A method for measuring the thickness of a pipe wall, comprising the steps of:
   emitting an ultrasonic signal into the pipe wall at a frequency and receiving reflected ultrasonic signals resulting from the emitted signal, wherein the frequency is such that the reflected ultrasonic signals are not localized in time, and providing a sensor signal representative of the received reflected signals, including a first received reflected signal and a second received reflected signal;
   providing a first model signal representative of the first received reflected signal and a second model signal representative of the second received reflected signal;
   correlating the received reflected signals to the model signals, including varying a time delay between the model signals, until the model signals separated by the time delay substantially agree with the received reflected signals; and
   determining the thickness of the pipe wall using the time delay.

* * * * *